United States Patent [19]

Scherkenbeck et al.

[11] Patent Number: 5,216,006
[45] Date of Patent: * Jun. 1, 1993

[54] FUNGICIDAL AZOLYL-PROPANOL DERIVATIVES

[75] Inventors: Je,uml/u/ rgen Scherkenbeck, Leverkusen; Thomas Himmler, Cologne; Klaus Stroech, Solingen; Stefan Dutzmann, Hilden; Gerd Hänssler, Leverkusen; Heinz-Wilhelm Dehne, Monheim, all of Fed. Rep. of Germany

[73] Assignee: Bayer Aktiengesellschaft, Leverkusen, Fed. Rep. of Germany

[*] Notice: The portion of the term of this patent subsequent to Nov. 10, 2009 has been disclaimed.

[21] Appl. No.: 709,540

[22] Filed: Jun. 3, 1991

[30] Foreign Application Priority Data

Jun. 13, 1990 [DE] Fed. Rep. of Germany ....... 4018927

[51] Int. Cl.$^5$ .................. A01N 43/653; C07D 249/08
[52] U.S. Cl. ..................... 514/383; 514/184; 548/101; 548/267.8; 548/268.6
[58] Field of Search ............. 548/101, 267.8, 268.6; 514/184, 383

[56] References Cited

U.S. PATENT DOCUMENTS

| | | | |
|---|---|---|---|
| 4,551,469 | 11/1985 | Parry et al. | 514/383 |
| 4,719,307 | 1/1988 | Lantzsch et al. | 548/267.8 |
| 4,871,389 | 10/1989 | Elliott et al. | 548/267.8 |
| 4,913,727 | 4/1990 | Stroech et al. | 71/92 |
| 4,980,367 | 12/1990 | Cuomo et al. | 548/268.6 |
| 5,025,031 | 6/1991 | Lantzsch et al. | 548/267.8 |
| 5,034,052 | 7/1991 | Stroech et al. | 548/267.8 |

OTHER PUBLICATIONS

E. J. Corey et al, "Dimethyloxosulfonium Methylide . . .", J. Amer. Chem. Soc. vol. 87 (1965, pp. 1353–1364.
T. Kutsuma et al, "A Convenient Method for a Preparation of Oxiranes . . . ", Heterocycles vol. 8, (1977, pp. 397–401.

*Primary Examiner*—Patricia L. Morris
*Attorney, Agent, or Firm*—Sprung Horn Kramer & Woods

[57] ABSTRACT

Fungicidal azolyl-propanols of the formula

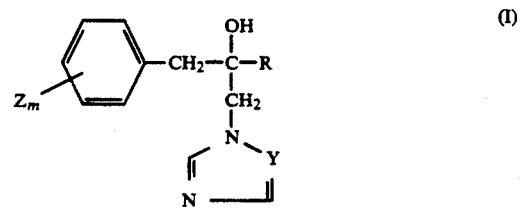

in which
R represents halogenoalkyl, halogenoalkenyl, a 2-phenoxy-isopropyl radical,

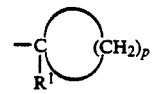

or

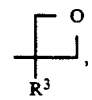

Y represents nitrogen or a CH group,
Z represents halogen, alkyl, halogenoalkyl, alkoxy, halogenoalkoxy, cyano, phenoxy, halo-phenoxy, or optionally substituted aryl,
m represents the number 0, 1, 2, or 3, and addition products thereof with acids and metal salts.

8 Claims, No Drawings

FUNGICIDAL AZOLYL-PROPANOL DERIVATIVES

The invention relates to new azolyl-propanol derivatives, to a process for their preparation, and to their use as fungicides.

It has already been disclosed that certain azolyl-propanol derivatives have fungicidal properties (cf. EP-OS (European Published Specification) 0,015,756 and EP-OS (European Published Specification) 0,297,345). The activity of these substances is good; however, it leaves something to be desired in some cases when low amounts are applied.

New azolyl-propanol derivatives of the formula

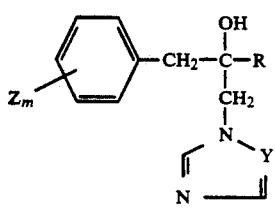

in which

R represents halogenoalkyl having 1 to 18 carbon atoms and 1 to 12 halogen atoms, halogenoalkenyl having 2 to 18 carbon atoms and 1 to 12 halogen atoms, or a radical of the formula

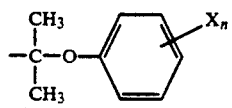

where

X represents alkyl having 1 to 6 carbon atoms, halogen, or halogenoalkyl having 1 to 4 carbon atoms and 1 to 5 halogen atoms, and n represents the numbers 0, 1, 2 or 3, or R represents a radical of the formula

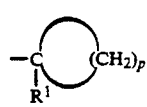

where $R^1$ represents n-propyl, vinyl, or phenyl which is optionally substituted by halogen and/or alkyl having 1 to 4 carbon atoms, and p represents the numbers 3, 4 or 5, or R represents a radical of the forrula

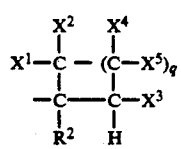

where $E^2$ represents hydrogen, halogen, methyl or ethyl,
$X^1$ represents halogen or trifluoromethyl,
$X^2$ represents halogen or trifluoromethyl,
$X^3$ represents hydrogen or halogen,
$X^4$ represents hydrogen or halogen,
$X^5$ represents hydrogen or halogen and
q represents the numbers 0, 1 or 2, or
R represents a radical of the formula

where $R^3$ represents alkyl having 1 to 4 carbon atoms, or halogen,

Y represents nitrogen or a CH group,

Z represents halogen, alkyl having 1 to 6 carbon atoms, halogenoalkyl having 1 to 6 carbon atoms and 1 to 13 halogen atoms, alkoxy having 1 to 6 carbon atoms, halogenoalkoxy having 1 to 6 carbon atoms and 1 to 13 halogen atoms, cyano, phenoxy which is optionally substituted by halogen, or aryl having 6 to 10 carbon atoms, it being possible for each of the aryl radicals to be substituted by halogen, alkyl having 1 to 4 carbon atoms, halogenoalkyl having 1 to 4 carbon atoms and 1 to 5 halogen atoms, alkoxy having 1 to 4 carbon atoms and/or halogenoalkoxy having 1 to 4 carbon atoms and 1 to 5 halogen atoms, and m represents the numbers 0, 1, 2 or 3, and their acid addition salts and metal salt complexes have now been found.

It has furthermore been found that azolyl-propanol derivatives of the formula (I) and their acid addition salts and metal salt complexes are obtained when oxiranes of the formula

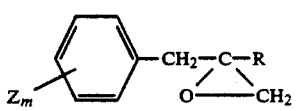

in which

R, Z and m have the abovementioned meanings, are reacted with azoles of the formula

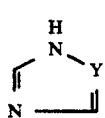

in which

Y has the abovementioned meaning, if appropriate in the presence of an acid-binding agent
and in the presence of a diluent, and, if desired, an acid or a metal salt is subsequently added onto the resulting compounds of the formula (I).

Finally, it has been found that the new azolyl-propanol derivatives of the formula (I) and their acid addition salts and metal salt complexes have very good fungicidal properties.

The substances according to the invention contain an asymmetrically substituted carbon atom. They can therefore be obtained in forms of optical isomers. The present invention relates to the individual isomers as well as to their mixtures.

Surprisingly, the substances according to the invention have better fungicidal properties than the previously known compounds of the same direction of action which are most similar as regards their constitution.

Formula (I) provides a general definition of the azolylpropanol derivatives according to the invention.

In the compounds of the formula given above,

R preferably represents halogenoalkyl having 1 to 6 carbon atoms and 1 to 6 fluorine, chlorine and/or bromine atoms, or halogenoalkenyl having 2 to 8 carbon atoms and 1 to 6 fluorine, chlorine and/or bromine atoms, particularly preferably halogenoalkyl having 1 to 4 carbon atoms and 1 to 5 fluorine, chlorine and/or bromine atoms, or halogenoalkenyl having 2 to 6 carbon atoms and 1 to 5 fluorine, chlorine and/or bromine atoms. Moreover, R represents a radical of the formula $$-\underset{CH_3}{\overset{CH_3}{\underset{|}{C}}}-O-\!\!\!\left\langle\!\!\!\bigcirc\!\!\!\right\rangle\!\!\!-X_n$$

where

X preferably represents alkyl having 1 to 4 carbon atoms, fluorine, chlorine or halogenoalkyl having 1 or 2 carbon atoms and 1 to 3 fluorine and/or chlorine atoms, and particularly preferably methyl, ethyl, fluorine, chlorine, trifluoromethyl or trichloromethyl, and n represents the numbers 0, 1 or 2.

Furthermore,

R represents a radical of the formula $$-\underset{R^1}{\overset{}{\underset{|}{C}}}\!\!\!\left\langle\!\!(CH_2)_p\!\!\right\rangle$$

where $R^1$ preferably represents n-propyl, vinyl, or phenyl which is optionally monosubstituted or disubstituted by identical or different substituents from the series comprising fluorine, chlorine, methyl and/or ethyl, and p represents the numbers 3, 4 or 5.

In addition,

R represents a radical of the formula $$\begin{array}{c}X^2\quad\; X^4\\ |\quad\quad\; |\\ X^1-C-(C-X^5)_q\\ |\quad\quad\; |\\ -C-\!-\!C-X^3\\ |\quad\quad\; |\\ R^2\quad\; H\end{array}$$

where $R^2$ preferably represents hydrogen, fluorine, chlorine, bromine, methyl or ethyl, $X^1$ preferably represents fluorine, chlorine or trifluoromethyl, $X^2$ preferably represents fluorine, chlorine or trifluoromethyl, $X^3$ preferably represents hydrogen, fluorine or chlorine, $X^4$ preferably represents hydrogen, fluorine or chlorine, $X^5$ preferably represents hydrogen, fluorine or chlorine and q represents the numbers 0, 1 or 2.

Finally,

R represents a radical of the formula $$-\!\!\!\left[\!\!\!\begin{array}{c}O\\ \\ R^3\end{array}\!\!\!\right]$$

where $R^3$ preferably represents methyl, ethyl, fluorine, chlorine or bromine.

Y represents nitrogen or a CH group.

Z preferably represents fluorine, chlorine, bromine, alkyl having 1 to 4 carbon atoms, halogenoalkyl having 1 to 4 carbon atoms and to 5 fluorine and/or chlorine atoms, alkoxy having 1 to 4 carbon atoms, halogenoalkoxy having 1 to 4 carbon atoms and 1 to 5 fluorine and/or chlorine atoms, cyano, phenoxy which is optionally monosubstituted to trisubstituted by fluorine and/or chlorine, or represents phenyl or naphthyl, it being possible for each of the two last-mentioned radicals to be monosubstituted to trrsubstituted by identical or different substituents from the series comprising fluorine, chlorine, alkyl having 1 to 3 carbon atoms, halogenoalkyl having 1 or 2 carbon atoms and 1 to 5 fluorine and/or chlorine atoms, alkoxy having 1 to 3 carbon atoms or by halogenoalkoxy having 1 or 2 carbon atoms and 1 to 5 fluorine and/or chlorine atoms.

Z particularly preferably represents fluorine, chlorine, bromine, methyl, ethyl, trifluoromethyl, trichloromethyl, methoxy, ethoxy, trifluoromethoxy, trichloromethoxy, cyano, phenoxy which is optionally monosubstituted or disubstituted by fluorine and/or chlorine, or phenyl which is optionally monosubstituted or disubstituted by identical or different substituents from the series comprising fluorine, chlorine, methyl, ethyl, trifluoromethyl, trichloromethyl, methoxy, ethoxy, trifluoromethoxy or trichloromethoxy.

m represents the numbers 0, 1, 2 or 3.

If m in the formula (I) represents the numbers 2 or 3, the radicals representing Z can be identical or different.

Examples of azolyl-propanol derivatives of the formula (I) which may be mentioned are the substances listed in the table which follows.

TABLE 1

$$Z_m\!\!-\!\!\!\left\langle\!\!\!\bigcirc\!\!\!\right\rangle\!\!-CH_2\!\!-\!\!\underset{\underset{N\diagdown\!\!\diagup\!Y}{\overset{|}{CH_2}}}{\overset{OH}{\underset{|}{C}}}\!\!-R \qquad (I)$$

| $Z_m$ | R | Y |
|---|---|---|
| 2-Cl | Cl-C(CH$_3$)-Cl (cyclopropyl) | N |
| 2-Cl | cyclohexyl with H and CH=CH$_2$ | N |

TABLE 1-continued $$\underset{Z_m}{\overset{}{\underset{}{\bigcirc}}}-CH_2-\underset{\underset{CH_2}{|}}{\overset{OH}{\underset{|}{C}}}-R \qquad (I)$$

$$\underset{N}{\overset{}{\underset{}{\underset{||}{N}}}}\underset{}{\overset{}{\underset{}{\underset{}{N}}}}Y$$

| $Z_m$ | R | Y |
|---|---|---|
| 2-Cl | ▽—⌬—Cl | N |
| 2-Cl | ☐(cyclobutyl)—⌬—Cl | N |
| 2-Cl | ☐—C₃H₇-n | N |
| 2-Cl | —C(CH₃)₂—O—⌬—Cl | N |
| 2-Cl | ☐(with O)—C₂H₅ | N |
| 2-Cl | —C(Cl)=C(Cl)Cl | N |

Other preferred substances according to the invention are addition products of acids and those azolyl-propanol derivatives of the formula (I) in which R, Y, Z and m have the meanings which have already been mentioned as being preferred for these radicals and the index m.

The acids which can be added on preferably include hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid and also sulphonic acids such as, for example, p-toluene-sulphonic acid, 1,5-naphthalenedisulphonic acid or camphorsulphonic acid.

Other preferred compounds according to the invention are addition products of salts of metals of main groups II to IV and subgroups I and II and IV to VIII of the Periodic System of the Elements and those azolyl-propanol derivatives of the formula (I) in which R, Y, Z and m have the meanings which have already been mentioned as being preferred for these radicals and the index m.

From amongst these, salts of copper, zinc, manganese, magnesium, tin, iron and of nickel are particularly preferred. Suitable anions of these salts are those which are derived from those acids which lead to physiologically acceptable addition products.

Particularly preferred acids of this type in this connection are the hydrohalic acids such as, for example, hydrochloric acid and hydrobromic acid, furthermore phosphoric acid, nitric acid and sulphuric acid.

If 2-(4-fluoro-benzyl)-2-(2,2-difluoro -1-methyl-cyclopropyl)-oxirane and 1,2,4-triazole are used as starting substances, the course of the process according to the invention can be illustrated by the following equation:

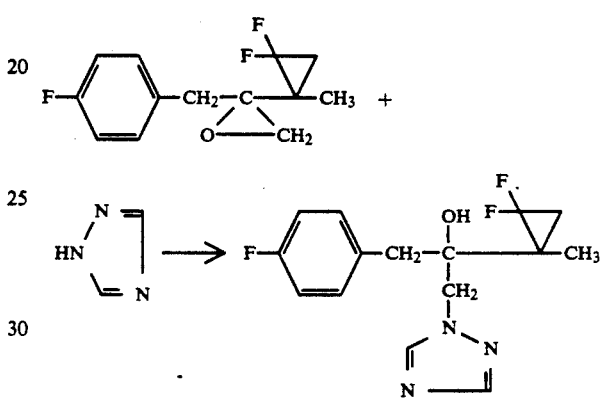

Formula (II) provides a general definition of the oxiranes required as starting substances in the process according to the invention.

The oxiranes of the formula (II) were hitherto unknown. They can be prepared by reacting benzyl ketones of the formula

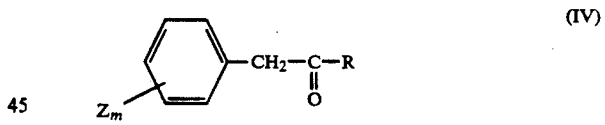

in which

R, Z and m have the abovementioned meanings, either

α) with dimethyloxosulphonium methylide of the formula

(V)

or

β) with dimethylsulphonium methylide of the formula

(VI)

in the presence of a diluent.

The benzyl ketones of the formula (IV) are only known in some cases to date. They can be prepared by a) reacting, in a first step, benzyl chlorides of the formula

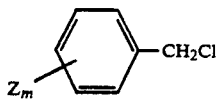

(VII)

in which

Z and m have the abovementioned meanings, with an excess of zinc powder in the presence of a diluent at temperatures between 30° C. and 200° C. under a protective gas atmosphere, removing the excess zinc powder, and then b) reacting, in a second step, the resulting benzyl derivatives of the formula

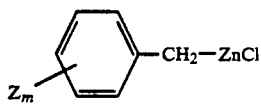

(VIII)

in which

Z and m have the abovementioned meanings, with acid chlorides of the formula

 R—CO—Cl        (IX)

in which

R has the abovementioned meaning,
in the presence of a palladium catalyst and in the presence of a diluent at temperatures between 0° C. and 150° C. under a protective gas atmosphere.

The benzyl chlorides of the formula (VII) which are required as starting substances for carrying out the above process for the preparation of benzyl ketones of the formula (IV) are known or can be prepared in a simple manner by processes known in principle.

The acid chlorides of the formula (IX) which are required as reactants for carrying out the above process for the preparation of benzyl ketones of the formula (IV) are also known or can be prepared in a simple manner by processes known in principle.

When carrying out the above process for the preparation of benzyl ketones of the formula (IV), the zinc powder can be employed in various grain sizes. Zinc dust or zinc powder of small particle size can preferably be used.

Suitable palladium catalysts for carrying out the above process for the preparation of benzyl ketones of the formula (IV) are all palladium(II) salts, palladium-(II) complexes and palladium(0) complexes which are customary for such purposes. The following can preferably be used: palladium(II) chloride, palladium(II) acetate, bis(triphenylphosphine)-palladium(II) chloride, bis(benzonitrile)-palladium(II) chloride and tetrakis (triphenylphosphine)-palladium(O). Diluents which can be employed in the preparation of benzyl ketones of the formula (IV) by the above process, for carrying out step one as well as step two, are all customary inert, organic solvents. The following can preferably be used: ethers such as diethyl ether, tert.-butyl methyl ether, tert.-amyl methyl ether, tetrahydrofuran, 2,5-dimethyl-tetrahydrofuran, ethylene glycol dimethyl ether, ethylene glycol tert.-butyl methyl ether, diethylene glycol diethyl ether and dioxane, furthermore nitriles such as acetonitrile, and in addition amides such as dimethylformamide and dimethylacetamide. The solvents are preferably employed in dry form.

Suitable protective gases for carrying out the process for the preparation of benzyl ketones of the formula (IV), in step one as well as in step two, are all customary inert gases. Helium, argon and nitrogen can preferably be used.

When carrying out the process for the preparation of benzyl ketones of the formula (IV), the reaction temperatures can be varied within a substantial range, in step one as well as in step two. In step one, the process is generally carried out at temperatures between 30° C. and 200° C., preferably between 50° C. and 150° C., and in step two the process is generally carried out at temperatures between 0° C. and 150° C., preferably between 20° C. and 100° C.

In the case of the above process for the preparation of benzyl ketones of the formula (IV), the reaction times can also be varied within a substantial range, when carrying out step one as well as step two. In step one, the reaction times are generally between 0.5 and 4 hours, preferably between 1 and 3 hours. In step two, the reaction times are generally between 0.1 and 5 hours, preferably between 0.5 and 3 hours.

The process for the preparation of benzyl ketones of the formula (IV) is generally carried out under atmospheric pressure. However, it is also possible to carry out the process under reduced or increased pressure.

When carrying out step one of the above process for the preparation of benzyl ketones of the formula (IV), the benzyl chloride of the formula (VII) is reacted with an excess of zinc. In general, between 1.05 and 3 mols. preferably between 1.1 and 2.5 mols. particularly preferably between 1.25 and 2.0 mol of zinc are generally employed per mol of benzyl chloride of the formula (VII).

When carrying out step two of the above process for the preparation of benzyl ketones of the formula (IV), the amount of palladium catalyst can be varied within a certain range. In general, between 0.001 and 1 mol %, preferably between 0.0025 and 0.1 mol %, particularly preferably between 0.005 and 0.05 mol %, of palladium catalyst are generally employed per mol of acid chloride of the formula (IX). When carrying out the above process for the preparation of benzyl ketones of the formula (IV), the ratio of benzyl chloride of the formula (VII) to acid chloride of the formula (IX) can be varied within a substantial range. Between 1.01 and 1.25 mols, preferably between 1.05 and 1.2 mols, of benzyl chloride of the formula (VII) are generally employed per mol of acid chloride of the formula (IX).

When step one of the above process for the preparation of benzyl ketones of the formula (IV) is complete, the excess zinc can be separated off by customary methods. For example, the zinc can be removed by filtration or centrifugation, or alternatively, by pumping off the supernatant solution once the zinc has settled.

When carrying out the above process for the preparation of benzyl ketones of the formula (IV), a specific procedure is followed in which the benzyl chloride of the formula (VII) is first reacted with the zinc in a suitable diluent under a protective gas atmosphere, the excess zinc is then separated off, the acid chloride of the formula (IX) and the palladium catalyst are added to the solution which remains, and the mixture is allowed to react until the reaction is complete. Working-up is carried out by customary methods. In general, a procedure is followed in which the reaction mixture is filtered, if appropriate, and then water and, if appropriate, dilute aqueous mineral acid is added, if appropriate after the mixture has been diluted with an organic solvent which is sparingly miscible with water, and the organic phase is separated off, dried and concentrated. The product which remains can be freed from any impurities which may still be present by customary methods such as, for example, distillation or recrystallization.

Dimethyloxosulphonium methylide of the formula (V), which is required as a reactant for carrying variant (α) of the process for the preparation of oxiranes of the formula (II), is known (cf. J. Am. Chem. Soc. 87, 1363-1364 (1965)). In the above reaction, it is processed in the freshly prepared state, by preparing it in situ by reacting trimethyloxosulphoniu iodide with sodium hydride or sodium amide, in particular with potassium tert.-butylate or sodium methylate, or by reaction of trimethyloxosulphonium chloride with aqueous sodium hydroxide solution, in each case in the presence of a diluent.

Dimethylsulphonium methylide of the formula (VI), which is also suitable as a reactant for carrying out variant (β) of the process for the preparation of oxiranes of the formula (II), is likewise known (cf. Heterocycles 8, 397 (1977)). In the above reaction, it is likewise employed in the freshly prepared state, for example by preparing it in situ from trimethylsulphonium halide or trimethylsulphonium methylsulphate, in the presence of a strong base such as, for example, sodium hydride, sodium amide, sodium methylate, potassium tert.-butylate or potassium hydroxide, in the presence of a diluent such as tert.-butanol or dimethyl sulphoxide.

Suitable diluents for carrying out the above process for the preparation of oxiranes of the formula (II) are inert organic solvents. The following can preferably be used: alcohols such as tert.-butanol, ethers such as tetrahydrofuran or dioxane, furthermore aliphatic and aromatic hydrocarbons such as benzene, toluene or xylene, and also strongly polar solvents such as dimethyl sulphoxide.

When carrying out the above process for the preparation of oxiranes of the formula (II), the reaction temperatures can be varied within a substantial range. In general, the process is carried out at temperatures between 0° C. and 100° C., preferably between 10° C. and 60° C.

When carrying out the above process for the preparation of oxiranes of the formula (II), 1 to 3 mols of dimethyloxosulphcnium methylide of the formula (V) or of dimethylsulphonium methylide of the formula (VI) are generally employed per mol of benzyl ketone of the formula (IV). The oxiranes of the formula (II) are isolated by customary methods.

Suitable acid-binding agents for carrying out the process according to the invention are all customary inorganic and organic bases. The following can preferably be used: alkali metal carbonates such as sodium carbonate and potassium carbonate, furthermore alkali metal hydroxides such as sodium hydroxide and potassium hydroxide, in addition alkali metal alcoholates such as sodium methylate, sodium ethylate, potassium methylate and potassium ethylate, as well as potassium tert.-butylate, and furthermore lower tertiary alkylamines, cycloalkylamines and aralkylamines such as, in particular, triethylamine.

Suitable diluents for carrying out the process according to the invention are all customary inert organic solvents. The following can preferably be used: nitriles such as acetonitrile, furthermore aromatic hydrocarbons such as benzene, toluene and dichlorobenzene, in addition formamides, such as dimethylformamide, as well as strongly polar solvents such as dimethyl sulphoxide and hexamethylphosphoric triamide.

When carrying out the process according to the invention, the reaction temperatures can be varied within a substantial range. In general, the process is carried out at temperatures between 0° C. and 200° C., preferably between 50° C. and 150° C.

When carrying out the process according to the invention, 1 to 4 mols of azole of the formula (III) and 1 to 2 mols of base are preferably employed per mol of oxirane of the formula (II). The end products are isolated in a customary manner.

The azolyl-propanol derivatives of the formula (I) according to the invention can be converted into acid addition salts or metal salt complexes. Suitable acids for the preparation of acid addition salts of the compounds of the formula (I) are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if appropriate, purified by washing with an inert organic solvent.

Preferred salts of metals which are suitable for preparing metal salt complexes of the compounds of the formula (I) are those which have already been mentioned as preferred metal salts in connection with the description of the metal salt complexes according to the invention.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if desired, they can be purified by recrystallization. The active compounds according to the invention have a powerful microbicidal action and can be employed as fungicides.

Fungicides are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae*; Pseudomonas species, such as *Pseudomonas lachrymans*; Erwinia species, such as *Erwinia amylovora*; Pythium species, such as *Pythium ultimum*; Phytophthora species, such as *Phytophthora infestans*; Pseudoperonospora species, such as *Pseudoperonospora humuli* or *Pseudoperonospora cubense*; Plasmopara species, such as Plasmopara viticola; Peronospora species, such as *Peronospora pisi* or *P. brassicae*; Erysiphe species, such as Erysiphe graminis; Sphaerotheca species, such as *Sphaerotheca fuliginea*; Podosphaera species, such as *Podosphaera leucotricha*; Venturia species, such as *Venturia inaequalis*; Pyrenophora species, such as *Pyrenophora teres* or *P graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus*; Puccinia species, such as *Puccinia recondita*; Tilletia species, such as *Tilletia caries*; Ustilago species, such as *Ustilago nuda* or *Ustilago avenae*; Pellicularia species, such as *Pellicularia sasakii*; Pyricularia species, such as *Pyricularia oryzae*; Fusarium species, such as *Fusarium culmorum*; Botrytis species, such as *Botrytis cinerea*; Septoria species, such as *Septoria nodorum*; Leptosphaeria species, such as *Leptosphaeria nodorum*; Cercospora species, such as *Cercospora canescens*; Alternaria species, such as *Alternaria brassicae* and Pseudocercosporella species, such as *Pseudocercosporella hrrpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* and Pellicularia sasakii in rice and for combating cereal diseases such as *Leptosphaeria nodorum*, Erysiphe and Pseudocercosporella. In addition, the substances according to the invention have a very good action against Venturia, Sphaerotheca and Botrytis.

The substances according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albuxyn hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils. It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated. When employing the substances according to the invention, the applicaiton rate can be varied within a substantial range depending on the method of application. For exmaple, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, required at the place of action.

The preparation adn the use of the substances according to the invention can be seen from the examples which follow.

PREPARATION EXAMPLES

EXAMPLE 1

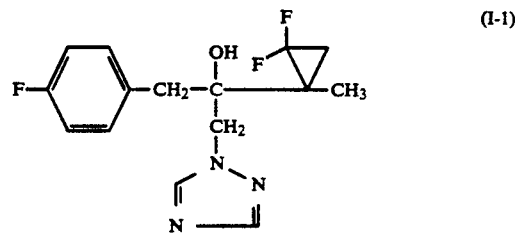

(I-1)

A solution of 6.3 g (0.026 mol) of 2-(4-fluorobenzyl)-(2,2-difluoro-1-methyl-cyclopropyl)-oxirane in 5 ml of dimethylformamide is added dropwise with stirring at 80° C. to a mixture of 4.6 g (0.066 mol) of 1,2,4-triazole and 0.5 g (0.0045 mol) of potassium tert.-butylate in 10 ml of dimethylformamide. When the addition is complete, the reaction mixture is stirred for 8 hours at 80° C. The solvent is subsequently stripped off under reduced pressure and the residue which remains is dissolved in ethyl acetate. The organic solution is washed with water, dried over sodium sulphate and concentrated under reduced pressure. The residue is chromatographed on silica gel using dichloromethane as the eluent. After the eluate has been evaporated, 1.7 g (21% of theory) of 1-(4-fluoro- phenyl)-2-(2,2-difluoro-1-methyl-cyclopropyl)3-(1,2,4-triazol-1-yl)-propan-2-ol are obtained in the form of a solid substance of melting point 114° C.

Preparation of starting substances:

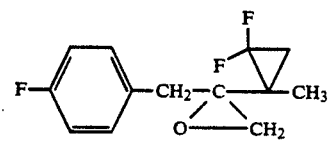 (II-1)

20 ml of absolute dimethyl sulphoxide are added dropwise to a mixture of 5.31 g (0.0241 mol) of trimethylsulphoxonium iodide and 0.79 g (0.0329 mol) of sodium hydride (80%) at 10° C. under a nitrogen atmosphere. When the addition is complete, the mixture is allowed to warm to room temperature in the course of 10 minutes, and a solution of 5 g (0.0219 mol) of 4-fluorobenzyl 2,2-difluoro-1-methyl-cyclopropyl ketone in 10 ml of absolute dimethyl sulphoxide is then added dropwise with stirring. Stirring is continued for 4 hours at 40° C. The reaction mixture is then poured onto ice-water. The mixture which forms is extracted three times using cyclohexane. The combined organic phases are dried over sodium sulphate and concentrated under reduced pressure. In this manner, 6.3 g of 2-(4-fluoro-benzyl)2-(2,2-difluoro-1-methyl-cyclopropyl)-oxirane are obtained, which is used for further reaction without additional purification.

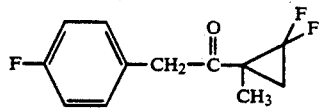 (IV-1)

A mixture of 6.5 g (100 mmol) of zinc powder, 9.55 g (66 mmol) of 4-fluorobenzyl chloride and 75 ml of dry ethylene glycol dimethyl ether is refluxed for 1 hour under a nitrogen atmosphere. The reaction mixture is subsequently filtered under nitrogen. 6.9 g (44.6 mmol) of 2,2-difluoro-1-methyl-cyclopropane-carboxylic acid chloride and 21 mg (0.07 mol %) of bis-(triphenylphosphine)palladium(II) chloride are added to the filtrate, and the mixture is refluxed for 1.5 hours under a nitrogen atmosphere. The reaction mixture is subsequently filtered under nitrogen. The filtrate is diluted with toluene, the mixture is extracted by shaking in succession with dilute aqueous hydrochloric acid and water, and the organic phase is dried and concentrated by stripping off the solvent under reduced pressure. The residue which remains is subjected to a distillation. In this manner, 8.8 g (85% of theory) of 4-fluorobenzyl (2,2-difluoro-1-methyl)-cyclopropyl ketone are obtained in the form of an oil.

$^1$H-NMR(200 MHz, CDCl$_3$): δ=1.2-1.35 (m; 1H), 1.5-1.6 (m; 3H), 2.25-2.4 (m; 1H), 3.8 (d, J=17 Hz; 1H), 3.84 (d, J=17 Hz; 1H), 6.9-7.2 (m; 4H) ppm.

The substances listed in the following examples are also prepared following the method given in Example 1.

EXAMPLE 2

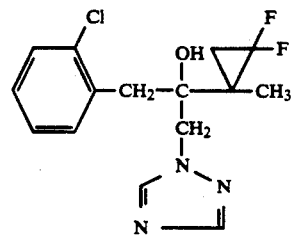 (I-2)

$^1$H-NMR (250 MHz, CDCl$_3$): δ=1.5 (t; 3H), 3.3 (AB system; 2H), 4.3 (AB system; 2H); 7.2-7.6 (H arom., 7.9 (s, 1H), 8.1 (s; 1H)

EXAMPLE 3

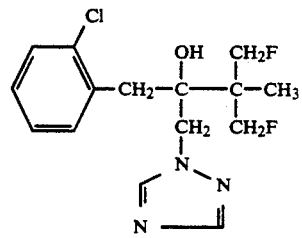 (I-3)

$^1$H-NMR (250 MHz CDCl$_3$) δ=1.0 (t; 3H), 3.3 (A,B system; 2H), 4.2-4.8 (m), 7.2-7.5 (H arom.), 7.8 (s; 1H), 7.9 (s, 1H)

EXAMPLE 4

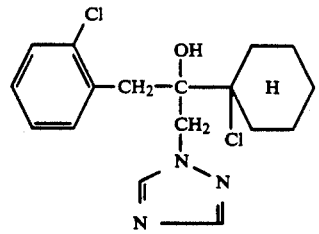 (I-4)

Melting point: 124° C.
The substances liste din the following Table 2 are also prepared according to the method given in Exmaple 1.

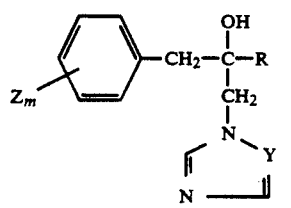 (I)

TABLE 2

| Ex. No. | $Z_m$ | R | Y | Physical constants |
|---|---|---|---|---|
| 5 | 2-Cl, 4-F | 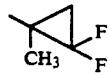 | N | $^1$H-NMR(200 MHz, CDCl$_3$) δ = 1.4 (m, 3H, CH$_3$), 3.2 (AB-system, 2H) 4.3 (AB-system, 2H), 7.0–7.4 (m, 3H), 7.9 (s, 1H), 8.1 (s, 1H). |
| 6 | 2-Cl | 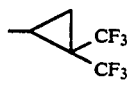 | N | $^1$H-NMR (200 MHz, CDCl$_3$) δ = 3.35 (s, 2H), 3.9 (s, 1H, OH), 4.3 (AB-system, 2H), 7.2–7.5 (m, 4H), 7.9 (s, 1H), 8.1 (s, 1H) |
| 7 | 2-Cl | 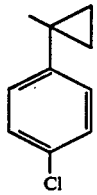 | N | $^1$H-NMR (200 MHz, CDCl$_3$); δ = 3.3 (AB-system, 2H) 4.2 (AB-system, 2H), 4.4 (s, 1H, OH), 7.1–7.5 (m, 4H), 7.9 (s, 1H), 8.1 (s, 1H). |
| 8 | 4-F | 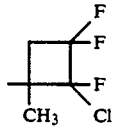 | N | $^1$H-NMR (200 MHz, CDCl$_3$); δ = 1.7 (d, 3H, CH$_3$), 3.1 (AB-system, 2H) 4.2 (AB-system, 2H), 7.0–7.3 (AB-System, 2H), 7.8 (s, 1H), 8.1 (s, 1H). |
| 9 | 2-Cl | 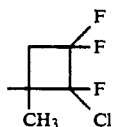 | N | $^1$H-NMR (200 MHz, CDCl$_3$); δ = 1.5 (d, 3H, CH$_3$), 3.0 (AB-system, 2H) 4.5 (AB-system, 2H), 7.0–7.5 (m, 4H), 7.8 (s, 1H), 8.1 (s, 1H) |
| 10 | 2-Cl, 4-F | 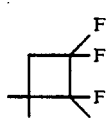 | N | $^1$H-NMR (200 MHz, CDCl$_3$); δ = 1.5 (d, 3H, CH$_3$), 3.0 (AB-System, 2H), 4.4 (AB-system, 2H), 6.8–7.6 (m, 3H), 7.9 (s, 1H), 8.7 (s, 1H) |
| 11 | 2-Cl | 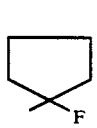 | N | $^1$H-NMR (200 MHz, CDCl$_3$); δ = 3.3 (AB-System, 2H), 4.3 (AB-system, 2H), 4.7 (s, 1H, OH), 7.1–7.6 (m, 4H), 7.8 (s, 1H), 8.0 (s, 1H) |
| 12 | 2-Cl | 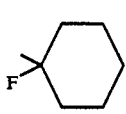 | N | M.p.: 106–107° C. |
| 13 | 4-Cl | 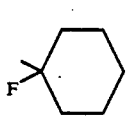 | N | $^1$H-NMR (200 MHz, CDCl$_3$); δ = 2.9 (AB-system, 2H), 3.7 (s, 1H), 4.2 (AB-system, 2H), 7.1–7.3 (m, 4H), 7.8 (s, 1H), 8.0 (s, 1H) |
| 14 | 2-Cl | 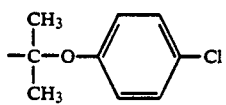 | N | $^1$H-NMR (200 MHz, CDCl$_3$); δ = 1.2 (s, 3H, CH$_3$), 1.3 (s, 3H, CH$_3$), 3.3 (AB-System, 2H), 4.9 (AB-System, 2H), 6.8–7.5 (m, 8H), 7.8 (s, 1H), 7.9 (s, 1H) |
| 15 | 2-Cl | 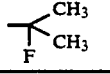 | N | $^1$H-NMR (200 MHz, CDCl$_3$); δ = 1.3 (d, 3H, CH$_3$), 1.5 (d, 3H, CH$_3$), 3.2, (AB-System, 2H) 4.3 (AB-system, 2H), 7.1–7.5 (m, 4H), 7.8 (s, 1H), 7.9 (s, 1H) |

The benzylketones of the formula (IV) listed in the following Table 3 are also prepared according to the method given in Example 1.

TABLE 3

$$\text{(IV)} \quad Z_m\text{-C}_6H_4\text{-CH}_2\text{-C(=O)-R}$$

| Ex. No. | Compound No. | $Z_m$ | R | Physical constants |
|---|---|---|---|---|
| 16 | IV-2 | 2-Cl | 1-methyl-2,2-difluorocyclopropyl | $^1$H-NMR (200 MHz, CDCl$_3$); δ = 1.2–1.4 (m; 1H), 1.6 (m; 3H), 2.25–2.45 (m; 1H), 3.9 (d, J ≃ 18 Hz; 1H), 4.0 (d, J ≃ 18 Hz; 1H), 7.1–7.45 (m; 4H) ppm |
| 17 | IV-3 | 2-Cl | −C(CH$_3$)$_2$−CH$_2$Cl | $^1$H-NMR (200 MHz, CDCl$_3$); δ = 1.34 (s, 6H), 3.65 (s; 2H); 3.98 (s; 2H), 7.2–7.5 (m; 4H) ppm |
| 18 | IV-4 | 2-Cl | −C(CH$_3$)$_2$Cl | $^1$H-NMR (200 MHz, CDCl$_3$); δ = 1.78 (s; 6H), 4.25 (s; 2H), 7.1–7.4 (m; 4H) ppm |
| 19 | IV-5 | 2-Cl | 1-methyl-2,2-dichlorocyclopropyl | $^1$H-NMR (200 MHz, CDCl$_3$); δ = 1.35 (d, J ≃ 7Hz; 1H), 1.73 (s; 3H), 2.29 (d, J ≃ 7Hz; 1H), 3.9 (d, J ≃ 17.5 Hz; 1H), 4.3 (d, J ≃ 17.5 Hz, 1H), 7.1–7.4 (m; 4H) ppm |
| 20 | IV-6 | 2-Cl | −C(CH$_3$)(CH$_2$F)$_2$ | $^1$H-NMR (200 MHz, CDCl$_3$); δ = 1.3 (t, J ≃ 1 Hz, 3H), 3.99 (d, J ≃ 20 Hz; 1H), 4.01 (d, J ≃ 20 Hz; 1H), 4.6 (ddd, J$_1$ ≃ 47 Hz, J$_2$ ≃ 9.5 Hz, J$_3$ ≃ 2Hz; 4H), 7.1–7.4 (m; 4H) ppm |
| 21 | IV-7 | 2-Cl | 1-vinylcyclohexyl | $^1$H-NMR (200 MHz, CDCl$_3$); δ = 1.3–2.2 (m; 10H), 3.90 (d, J ≃ 21 Hz; 1H), 3.92 (d, J ≃ 21 Hz; 1H), 5.2 (dd, J$_1$ ≃ 17 Hz, J$_2$ ≃ 1 Hz; 1H), 5.3 (dd, J$_1$ ≃ 11 Hz, J$_2$ ≃ 1Hz; 1H), 5.8 (dd, J$_1$ ≃ 17 Hz, J$_2$ ≃ 11 Hz; 1H), 7.0–7.4 (m; 4H) ppm |
| 22 | IV-8 | 2-Cl | −CH(Br)−CH$_3$ | $^1$H-NMR (200 MHz, CDCl$_3$); δ = 1.75 (d, J ≃ 7Hz; 3H), 4.13 (s; 2H), 4.5 (q, J ≃ 7 Hz; 1H), 7.2–7.4 (m; 4H) ppm |
| 23 | IV-9 | 2-Cl | −CH$_2$Cl | $^1$H-NMR (200 MHz, CDCl$_3$); δ = 3.99 (s; 2H), 4.18 (s; 2H), 7.2–7.5 (m; 4H) ppm |
| 24 | IV-10 | 2-Cl | 1-(4-chlorophenyl)cyclopropyl | $^1$H-NMR (200 MHz, CDCl$_3$); δ = 1.15–1.25 (m; 2H), 1.65–1.75 (m, 2H), 3.68 (s; 2H), 7.0–7.4 (m; 8H) ppm |
| 25 | IV-11 | 2-Cl | 1-(4-chlorophenyl)cyclobutyl | $^1$H-NMR (200 MHz, CDCl$_3$); δ = 1.8–2.05 (m; 2H), 2.3–2.55 (m; 2H), 2.8–3.0 (m; 2H), 3.63 (s; 2H), 6.9–7.4 (m; 8H) ppm |
| 26 | IV-12 | 2-Cl | 1-n-propylcyclobutyl | $^1$H-NMR (200 MHz, CDCl$_3$); δ = 0.8–1.0 (t; 3H), 1.1–1.3 (m; 2H), 1.7–2.0 (m; 6H), 2.35–2.6 (m, 2H), 3.81 (s; 2H) 7.1–7.4 (m; 4H) ppm |
| 27 | IV-13 | 2-Cl | 2,2-dichlorocyclopropyl | $^1$H-NMR (200 MHz, CDCl$_3$); δ = 1.8 (dd, J$_1$ ≃ 9 Hz, J$_2$ ≃ 6 Hz; 1H), 2.15 (dd, J$_1$ ≃ 7.5 Hz, J$_2$ ≃ 6 Hz, 1H), 2.8 (dd, J$_1$ ≃ 9 Hz, J$_1$ ≃ 7.5 Hz, 1H), 4.05 (s, 2H), 7.2–7.5 (m, 4H) ppm |

TABLE 3-continued $$\underset{Z_m}{\diagdown}\text{—CH}_2\text{—}\underset{\underset{O}{\|}}{\text{C}}\text{—R} \quad (IV)$$

| Ex. No. | Compound No. | $Z_m$ | R | Physical constants |
|---|---|---|---|---|
| 28 | IV-14 | 2-Cl | (cyclopentyl with two F on same carbon) | $^1$H-NMR (200 MHz, CDCl$_3$); δ = 1.6–2.4 (m; 6H), 3.25–3.5 (m; 1H), 3.97 (d, J = 6 Hz; 1H), 4.03 (d, J = 16 Hz; 1H), 7.1–7.5 (m; 4H) ppm |
| 29 | IV-15 | 2-Cl | (oxetane with CH$_3$) | $^1$H-NMR (270 MHz, CDCl$_3$); δ = 1.45 (s; 3H), 3.85 (s; 4H), 4.06 (s; 2H), 7.0–7.4 (m; 5H) ppm |
| 30 | IV-16 | 3-CF$_3$ | —CH$_2$Cl | Melting point: 42° C. |
| 31 | IV-17 | 2-CH$_3$, 4-F | —CH$_2$Cl | B.p.: 99–103/1 mbar |
| 32 | IV-18 | 2,6-Cl$_2$ | $\underset{\underset{\text{CH}_3}{\|}}{\overset{\overset{\text{CH}_3}{\|}}{-\text{C}-\text{F}}}$ | $^1$H-NMR (200 MHz, CDCl$_3$); δ = 1.56 (d, J = 21 Hz; 6H), 4.35 (m; 2H), 7.1–7.35 (m; 3H) ppm |

EXAMPLE A

Unicinula test (vine)/protective

Solvent: 4.7 parts by weight of acetone
Emulsifier: 0.3 parts by wieght of alkylarylpolyglycolether.

To produce a suitable preparation of acitve compound, 1 part by weight of active compound is mixed with the stated amounts of solvent and emulsifier, and the concentrate is diluted with water to the desired concentration.

To test for protective activity, young platns are sprayed with the preparation of active compound until dripping wet. After the spray coating has dried on, the plants are dusted with conidia of the Uncinula necator fungus.

The plants are then placed in a greenhouse at 23° to 24° C. and a relative humidity of about 75%.

Evaluation is carried out 14 days after the inoculation.

The compounds (1), (3), (5) and (14) according to the invention show a very good activity in this test.

EXAMPLE B

Venturia test(apple)/protective
Solvent: 4.7 parts by weight of acetone
Emulsifier: 0.3 parts by weight of alkylarylpolyglycolether To produce a suitable prpearation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

The compounds (3) and (5) according to the invention show a very good activity in this test.

EXAMPLE C

Botrytis test(bush bean)/protective
Solvent: 4.7 parts by weight of acetone
Emulsifier: 0.3 parts by weight of alkylarylpolyglycolether To produce a suitable prpearation of active compound, 1 part by weight of active compound is mixed with the stated amounts of solvent and emulsifier, and the concentrate is diluted with water to the desired concentration.

To test for protective actvity, young plants are sprayed with the preparation of active compund until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

The compounds (2), (3) and (5) accoridng to the invention show a very good activity in this test.

EXAMPLE D

Erysiphe test (barley)/protective
Solvent: 100 parts by weight of dimethylformamide
Emulsifier: 0.25 parts by weight of alkylarylpolyglycolether To produce a suitable preparation of active compound, 1 part by weight of active compound is mixed with stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the devleopment of powdery mildew pustules.

Evaluation is carried out 7 days after the inoculation.

The compounds (1) to (3), (5), (8), (9) and (11) to (15) according to the invention show a very good activity in this test.

EXAMPLE E

Pryicularia test (rice)/protective
Solvent: 12.5 parts by weight of acetone
Emulsifier: 0.3 parts by weight of alkylarylpolyglocolether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

The compounds (2), (3), (5) and (8) to (10) according to the invention show a very good activity in this test.

EXAMPLE F

Pyricularia test(rice)/systemic
Solvent: 12.5 parts by weight of acetone
Emulsifier: 0.3 parts by weight of alkylarylpolyglycolether To produce a suitable prepartion of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated wth an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

The compounds (1) to (3), (5) and (8) to (10) show a very good activity in this test.

EXAMPLE G

Pellicularia test(rice)
Solvent: 12.5 parts by weight of acetone
Emulsifier: 0.3 parts by weight of alkylarylpolyglycolether To produce a suitable preparation of active compound, 1 part by weight of active compound is mixed iwth the stated amount of solvent, and the concentrate is diluted with water and the stated amount of emulsifier, to the desired concentration.

To test for activity, young rice plants in the 3- to 4-leaf stage are sprayed until dripping wet. The plants remain in the greenhouse until they ahve dried off. The plants are then inoculated with Pellicularia sasakii and are placed at 25° C. and 100% relative atmospheric humidity.

The evaluation of the disease infestation is carried out 5 to 8 days after the inoculation.

The compounds (1) to (3), (5) and (8) to (10) according to the invention show a very good activity in this test.

It will be understood that the specification and examples are illustrative but not limitative of the present invention and that other embodiments within the spirt and scope of the invention will suggest themselves to those skilled in the art.

We claim:

1. An azolyl-propanol of the formula

[structure]

in which
R is a radical selected from the group consisting of

[structures]

Z is fluorine, chlorine, methyl or trifluoromethyl and m is 1 or 2,
or an addition product thereof with an acid or metal salt.

2. An azolyl-propanol according to claim 1, wherein such compound is 1-(4-fluoro-phenyl) -2-(2,2-difluoro-1-methyl-cyclopropyl) -3-(1,2,4-triazol-1-yl) propan-2-ol of the formula

[structure]

or an addition product thereof with an acid or metal salt.

3. An azolyl-propanol according to claim 1, wherein such compound is 1-(2-chloro-phenyl) -2-(2,2-difluoro-1-methyl-cyclopropyl) -3-(1,2,4-triazol-1-yl) -propan-2-ol of the formula

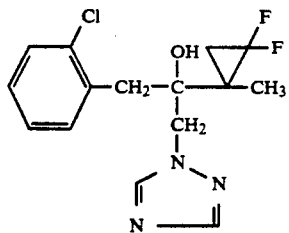

or an addition product thereof with an acid or metal salt.

4. An azolyl-propanol according to claim 1, wherein such compound is 1-(2,4-dichloro-phenyl) -2-(2,2-difluoro-1-methly-cyclopropyl) -3-(1,2,4-triazol-1-yl) propan-2-ol of the formula

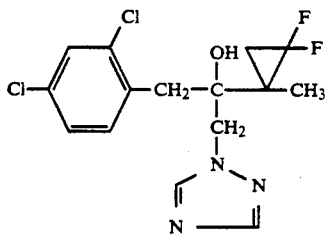

or an addition product thereof with an acid or metal salt.

5. An azolyl-propanol according to claim 1, wherein such compound is 1-(2-chloro-phenyl) -2-[2-(4-chloro-phenoxy) -isopropyl]-3-(1,2,4-triazol-1-yl) -propan-2-ol of the formula

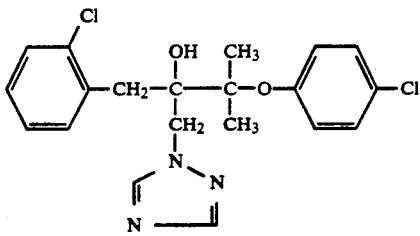

or an addition product thereof with an acid or metal salt.

6. A fungicidal composition comprising a fungicidally effective amount of a compound or addition product thereof accordng to claim 1 and a diluent.

7. A method of combating fungi which comprises applying to such fungi or to a locus from which it is desired to exclude such fungi a fungicidally effective amount of a compound or addition product thereof according to claim 1.

8. The method according to claim 7, wherein such compound is selected from the group consisting of
   1-(4-fluoro-phenyl)-2-(2,2-difluoro-1-methylcyclo-propyl)-3-(1,2,4-triazol-1-yl)-propan-2-ol,
   1-(2-chloro-phenyl)-2-(2,2-difluoro-1-methylcyclo-propyl) -3-(1,2,4-triazol-1-yl)-propan -2-ol,
   1-(2,4-dichloro-phenyl)2-(2,2-difluoro-1-methyl-cyclopropyl) -3-(1,2,4-triazol-1-yl) propan-2-ol, or
   1-(2-chloro-phenyl)-2-[2-(4-chlorophenoxy) isopropyl]-3-(1,2,4-triazol-1-yl) -propan-2-ol,
or an addition product thereof with an acid or metal salt.

* * * * *

UNITED STATES PATENT AND TRADEMARK OFFICE
CERTIFICATE OF CORRECTION

PATENT NO. : 5,216,006

DATED : June 1, 1993

INVENTOR(S) : Scherkenbeck, et al.

It is certified that error appears in the above-identified patent and that said Letters Patent is hereby corrected as shown below:

Title Page     [75] Inventors: 1st Inventor delete " Je,uml/u/rgen " and substitute -- Jurgen --

Title Page     U.S. PATENT DOCUMENTS: Delete " 5,025,031 " and substitute -- 5,025,030 --

Signed and Sealed this

First Day of November, 1994

*Attest:*

BRUCE LEHMAN

*Attesting Officer*     *Commissioner of Patents and Trademarks*